US008992227B2

(12) United States Patent
Al Bandar et al.

(10) Patent No.: US 8,992,227 B2
(45) Date of Patent: Mar. 31, 2015

(54) METHODS AND APPARATUS FOR ANALYSING THE BEHAVIOUR OF A SUBJECT

(75) Inventors: Zuhair Ghani Al Bandar, Sale (GB); David Anthony McLean, Manchester (GB); James Dominic O'Shea, Manchester (GB); Janet Alison Rothwell, Lytham St Annes (GB)

(73) Assignee: Manchester Metropolitan University (GB)

( * ) Notice: Subject to any disclaimer, the term of this patent is extended or adjusted under 35 U.S.C. 154(b) by 2203 days.

(21) Appl. No.: 10/475,922

(22) PCT Filed: Apr. 18, 2002

(86) PCT No.: PCT/GB02/01806
§ 371 (c)(1),
(2), (4) Date: May 3, 2004

(87) PCT Pub. No.: WO02/087443
PCT Pub. Date: Nov. 7, 2002

(65) Prior Publication Data
US 2004/0181145 A1      Sep. 16, 2004

(30) Foreign Application Priority Data
Apr. 28, 2001   (GB) .................................. 0110480.1

(51) Int. Cl.
*G09B 19/00*   (2006.01)
*A61B 5/16*    (2006.01)
*A61B 5/00*    (2006.01)

(52) U.S. Cl.
CPC .............. *A61B 5/164* (2013.01); *A61B 5/7267* (2013.01); *A61B 5/7232* (2013.01)

USPC .......................................... 434/236; 434/238

(58) Field of Classification Search
USPC ................................................ 434/236, 238
See application file for complete search history.

(56) References Cited

U.S. PATENT DOCUMENTS

| 5,204,703 | A |   | 4/1993 | Hutchinson et al. |
| 5,507,291 | A | * | 4/1996 | Stirbl et al. ................... 600/407 |
| 5,601,090 | A | * | 2/1997 | Musha .......................... 600/544 |
| 5,659,625 | A | * | 8/1997 | Marquardt ..................... 382/118 |

(Continued)

FOREIGN PATENT DOCUMENTS

| JP | 10-228295   |    | 8/2008 |
| WO | 99/53427    | A1 | 10/1999 |
| WO | 00/72256    | A2 | 11/2000 |

OTHER PUBLICATIONS

Otuska, Takahiro and Ohya, Jun. "Recognizing Multiple Persons' Facial Expressions Using HMM Based on Automatic Extraction of Significant Frames from Images Sequences." Proceedings of ICIP'97, Oct. 26-29, 1997.*

(Continued)

*Primary Examiner* — Robert J Utama
(74) *Attorney, Agent, or Firm* — Kaplan Breyer Schwarz & Ottesen, LLP

(57) ABSTRACT

There is disclosed a method for analyzing the behavior of a subject comprising the steps of: making one or more measurements or observations of the subject; coding the measurements or observations into a plurality of channels; and analyzing the channels using artificial intelligence, in order to output information relating to the psychology of the subject.

28 Claims, 2 Drawing Sheets

(56) References Cited

U.S. PATENT DOCUMENTS

| | | | | |
|---|---|---|---|---|
| 5,802,220 | A | * | 9/1998 | Black et al. .................. 382/276 |
| 5,867,257 | A | | 2/1999 | Rice et al. |
| 6,028,626 | A | * | 2/2000 | Aviv ............................ 348/152 |
| 6,092,058 | A | | 7/2000 | Smyth |
| 6,275,806 | B1 | * | 8/2001 | Pertrushin .................... 704/272 |
| 7,111,980 | B2 | * | 9/2006 | Pavlidis et al. ................ 374/45 |

OTHER PUBLICATIONS

Rowley et al "Neural Network-based Face Detection" PAMI Jan. 2008.*

Fu et al "Face Detection and Eye localization by neural network based color segmentation." IEEE 2000.*

Tsapatsoulis, et al. "Emotion Recognition and Synthesis Based on MPEG-4 FAPs" Copyright © 2002 John Wiley & Sons, Ltd. Department of Electrical Engineering, Linköping University, SE-581 83.*

International Preliminary Examination Report.

Zednek Prochazka et al., "A Method for Automatic Extraction of Motion Based Expression Features", D-2, vol. 1 JB1-D-2, No. 6, pp. 1150-1159.

* cited by examiner

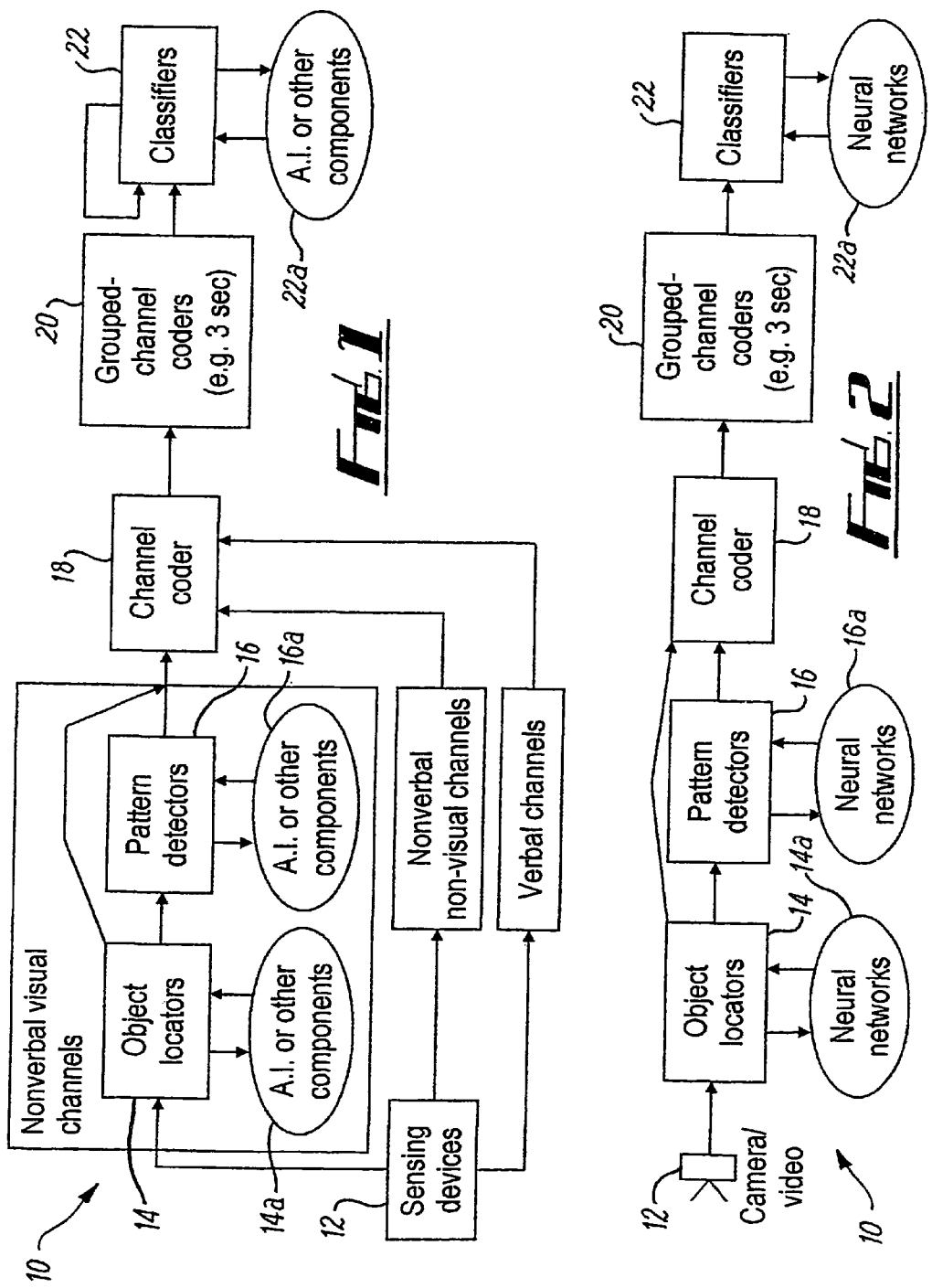

METHODS AND APPARATUS FOR ANALYSING THE BEHAVIOUR OF A SUBJECT

This invention relates to methods and apparatus for analysing the behaviour of a subject using artificial intelligence, with particular, but by no means exclusive, reference to the analysis of nonverbal visual behaviour of the subject using Artificial Neural Networks.

There is a great deal of interest in techniques for the psychological profiling of a subject in order to obtain information about the subject which the subject is either unwilling or genuinely unable to divulge. A prime example of this is the field of deception detection.

There are various deception detection devices (so called "lie detectors") which are used for this purpose. These devices are able to detect some cues which may indicate deception but, generally, they may not be suitable for measuring any other mental, behavioural and/or physical state.

U.S. Pat. No. 5,507,291 discloses a method for remotely determining information relating to a person's emotional state, in which waveform energy is wirelessly transmitted to a remotely located subject. Waveform energy emitted from the subject is detected and automatically analysed by comparing measured values with reference values, and information relating to the individual's emotional state is derived therefrom.

One well-known device, originally developed in the 1920s, is the Polygraph machine. In the USA, the device may be used for job interviews or insurance claims, and in New Mexico the results are admissible as evidence in a court of law. The Polygraph commonly records heart rate, breathing rate and sweat activity: tubes are fastened across the chest to monitor the breathing rate; a blood pressure cuff on one arm monitors the heart rate; the galvanic skin response at the tip of a finger monitors the sweat activity. An operator annotates a readout chart throughout the interview, so that the body responses can be linked to particular phrases or questions. It will be apparent to the skilled reader that the test is invasive.

The degree of credibility of the test is significantly influenced by the operator's level of skill when conducting the test and professional expertise when interpreting the charts, though there have been some attempts at automating the chart analysis. The result also depends upon the person undergoing the test—some persons are able to control their responses and thus skew the results of the test.

The Polygraph test relies upon just three measurements (channels) that are indicators of stress. It is possible that an innocent subject may feel stressed or embarrassed when, for example, accused of a crime. Any feelings of nervousness, embarrassment, fear, anger or misplaced guilt could create a stress response. Thus it is possible that responses from an innocent subject might be incorrectly interpreted as deception. Another problem is that a liar (or a truthful person) who knows a few simple tricks can control their stress responses and can thus fool the Polygraph operator. The effect of this is that the machine has a bias against a truthful person.

Another deception detector is a voice analyser device, which attempts to detect deception in real time by recording and measuring changes in the fundamental frequency of the voice. When a person is stressed, there is a drop in the amount of blood in the vocal chords. An involuntary interference of the nerves causes the vocal chords to produce a distorted sound wave of a slightly different frequency. Again, because this is a measurement (or channel) associated with stress, the subject may be able to control their stress response, especially if it is known that they are being monitored. It should be noted that the only application of the stress measurements taken by these devices is in the gauging of the truthfulness of the subject.

It is known that non-verbal, visual behaviour can be indicative of the psychological profile of a subject. By non-verbal "visual" behaviour it is meant external attributes of the subject which may be viewed by an on-looker, such as movements of the subject. This is to be contrasted with non-visual behaviour, such as heart beat rate and voice.

It is possible that Charles Darwin was the first scientist to investigate methodically patterns of non-verbal, visual behaviour in humans and animals. In a classic study, a "frame by frame" methodology of non-verbal behaviour analysis was expounded by Efron (Efron, D., Gesture and Environment, 1941, King's Crown, New York). In the frame by frame methodology, a film or video of the subject is recorded and a human judge observes and manually codes "channel" data from each frame ill the film. A channel is a well understood term in the field of psychological analysis, and represents a single aspect of the overall behaviour exhibited by the subject. A channel may comprise, for example, eye contact events, gaze, or body movements. Coding may simply comprise a record of whether a particular behaviour has taken place, or may comprise a measure of channel duration (over a number of frames), or may comprise some subjective opinion on the part of the judge.

Typically, multiple channels (multichannels) are chosen for a particular study, so the frame-by-frame method has to be performed a number of times, once for each channel. One human judge may do this by playing a video a number of times, or a number of judges, each responsible for one or two channels, may view the video.

The channel data may then be grouped into fixed time periods or time periods that coincide with some event, such as the answer to a question. The grouped data is then analysed by a person who has both experience in non-verbal behaviour and has experience of this type of analysis with the particular set of channels. It is hoped that patterns will be detected in the data that indicate some mental, behavioural or physical state.

There are a number of problems and disadvantages with the manual "frame by frame" technique which are discussed below.

Firstly, in the "frame by frame" technique, a human judge has to manually code each frame for every channel. The time requirement increases at least linearly with the number of channels and additional time is needed for the analysis stage. The final result would, at best, be available a few hours after the event. More likely, there would be a lapse of days or even weeks.

Secondly, the use of one or more highly trained judges over long periods and an experienced analyst is expensive.

Thirdly, for a particular psychological study, the relative importance of different channels is unknown. In the manual method, cost considerations will limit the number of channels actually collected and analysed. Channels chosen may be from a researcher's previous knowledge, from hearsay, or from literature references. Channels may be given the same level of importance or one channel may be given extra weight by the researcher.

In addition to the element of subjectivity, human judges may code channel information differently, be inconsistent or make errors due, for example, to fatigue. Different researchers may choose different channels, coding methods or analysis methods and therefore produce different results for the same frame sequence. Thus, analysis is inherently arbitrary.

Fourthly, when multiple channels are analysed over multiple same groupings, the analysis is particularly complex due to the high dimensionality of the data. With an increase in the number of channels, it is more likely that important patterns in the data are missed. Since humans can only concentrate fully on a limited number of channels, it is possible that important channels might be unwittingly ignored altogether.

From the foregoing, it will be apparent that the traditional frame by frame method of channel coding and subsequent analysis is time-consuming, costly, complex and error prone.

Furthermore, it will be apparent that there is a long felt need for improved methods and apparatus for analysing behaviour such as deception.

The present invention addresses these needs, problems and disadvantages.

For the avoidance of doubt, the term "nonverbal behaviour" is understood to refer to every behaviour exhibited by a subject excluding the meaning of words uttered by the subject. By "nonverbal visual behaviour" it is meant external attributes of the subject which may be viewed by an onlooker, such as movements of the subject. This is to be contrasted with "nonverbal, nonvisual behaviour", such as heart beat rate and voice pitch.

According to a first aspect of the invention there is provided an automatic method for analysing the behaviour of a subject comprising the steps of:
  making one or more measurements or observations of the subject;
  coding the measurements or observations into a plurality of channels; and
  analysing the channels using an automatic machine classification technique, in order to output information relating to the psychology of the subject.

There are numerous advantages associated with the method of the present invention. The method is automated, and extremely quick, being able to analyse the subject and provide the output information in, or close to, real time. By "automatic", it is meant that the technique is executed by machine, without human intervention. The method is highly cost effective, objective, consistent and reliable. Importantly, the present invention can accept and analyse a large number of channels without bias and without missing important behavioural information contained—even transitorily—within any given channel. This ability inter alia improves accuracy and reliability, because whilst a subject who is, for example, deceptive, may be able to control some of the behavioural channels, it is extremely unlikely that the subject would be able to control all channels consistently over a period of time.

In preferred embodiments, the automatic machine classification technique comprises artificial intelligence. However, other machine based techniques, such as statistical classification techniques, might be used. Such statistical techniques are purely mathematical in nature, and do not involve artificial intelligence. The classification techniques can be implemented using a computer or other form of microprocessor. The use of automatic machine classification techniques eliminates the disadvantages associated with the use of human judges.

The artificial intelligence used to analyse the channels may comprise an artificial Neural Network, genetic algorithm, decision tree, fuzzy logic, symbolic rules, machine learning and other forms of knowledge based systems. Pluralities and/or combinations of the above may be used.

Measurements of nonverbal behaviour of the subject may be made, which may be measurements of nonverbal visual behaviour of the subject and/or of nonverbal nonvisual behaviour of the subject. More specifically, observations of the movements of the subject may be made. Such observations are visual in nature, and thus have the advantage of being non-invasive for the subject. Another advantage is that a great deal of important information is revealed by the movements of a subject. Another advantage still is that a large number of channels can be coded from the movements of a subject. A further advantage is that a large number of channels can be coded from a single set of observations, eg, from a fame sequence obtained using a single video camera.

The observations of the movements of the subject may comprise a plurality of images of the subject; and the coding of the observations into the plurality of channels may comprise extraction of features from the images.

The channels may comprise eye movements (such as blinking, looking in a desired direction), facial movements (such as vertical, horizontal movement or tilting of the head and facial skin movement), or movements of the hands, legs, or torso of the subject. All of these are examples of movements of the subject.

Measurements or observations of other nonverbal behaviour may be made, either in addition to, or instead of, observations of the movements of the subject. Examples of such other measurements or observations are heart rate, sweat activity, breathing rate, brain wave patterns, thermal imaging, detection of any "wobble" in a chair in which the subject may be seated, and paralanguage measurements (Zuckerman, M., Driver, R. E., Telling Lies: verbal and nonverbal correlates of deception, in Mathematical integrations of nonverbal behaviour, Eds: A. W. SiegmanS. Feldstein, 1985). The choice of measurements or observations and the number of channels selected should be such that (in contrast to prior art techniques such as the Polygraph test discussed above) it is not possible for subjects to control their responses and thus "fool" the present technique.

Measurements or observations of verbal behaviour, i.e., the meaning of words uttered, may be made, either in addition to, or instead of, measurements or observations of nonverbal behaviour.

The channels may be analysed in order to establish whether the behaviour of the subject is deceptive. This is probably the psychological behaviour which is most difficult to detect. However, the present invention can detect deceptive behaviour with excellent accuracy.

In alternative applications, the channels may be analysed in order to establish the subject's mental, behavioural and/or physical state, examples of which comprise emotional traits such as stress, guilt, happiness, fear, confidence; personality traits such as introversion, extroversion, agreeableness, conscientiousness, openness to experience, emotional intelligence, bullying demeanor, compliant demeanor and medical traits such as true pain and psychopathic conditions.

According to a second aspect of the invention there is provided apparatus for automatically analysing the behaviour of a subject comprising:
  detection means for making one or more measurements or observations of the subject;
  coding means for coding the measurements or observations into a plurality of channels; and
  automatic machine classification means adapted to analyse the channels and output information relating to the psychology of the subject.

The detection means may make measurements or observations of nonverbal behaviour of the subject which may be measurements or observations of nonverbal visual behaviour of the subject. The detection means may make observations of the movements of the subject. The detection means may provide a plurality of images of the subject; and the coding means may comprise feature extraction means for extracting features from the images.

The coding means may code the observations into one or more channels relating to eye movements.

The coding means may code the observations into one or more channels relating to facial movements.

The coding means may code the observations into one or more channels relating to movements of the hands, legs or torso of the subject.

In general, the coding means may code the measurements or observations into one or more channels relating to nonverbal visual behaviour, nonverbal nonvisual behaviour and/or verbal behaviour.

The detection means may comprise one or more cameras or other image capturing means. Thus, for example, the coding means may code measurements or observations of nonverbal, nonvisual behaviour of the subject into one or more channels.

The detection means may comprise a microphone.

Preferably, the automatic machine classification means comprises artificial intelligence means which may comprise an artificial Neural Network, genetic algorithm, decision tree, fuzzy logic, symbolic rules, machine leaning and other forms of knowledge based systems. Pluralities and/or combinations of the above may be used. Other forms of automatic machine classification means, such as statistical classification means, might be used. A statistical classification means might comprise a microprocessor adapted, such as through a software implementation, to utilise statistical methods.

The artificial intelligence means may be adapted to establish whether the behaviour of the subject is deceptive.

The artificial intelligence means may be adapted to establish the subject's mental, behavioural and/or physical state, examples of which comprise emotional traits, such as stress, guilt, happiness, fear, confidence; personality traits such as introversion, extroversion, agreeableness, conscientiousness, openness to experience (intellect), emotional intelligence, bullying demeanor and compliant demeanor, and medical traits such as true pain and psychopathic conditions.

The artificial intelligence means may be adapted to output information concerning personality traits of the subject.

Embodiments of methods and apparatus in accordance with the invention will now be described with reference to the accompanying drawings, in which:—

FIG. 1 is a schematic diagram of apparatus according to the invention;

FIG. 2 is a schematic diagram of apparatus for analysing nonverbal visual behavioural.

Figure 3:
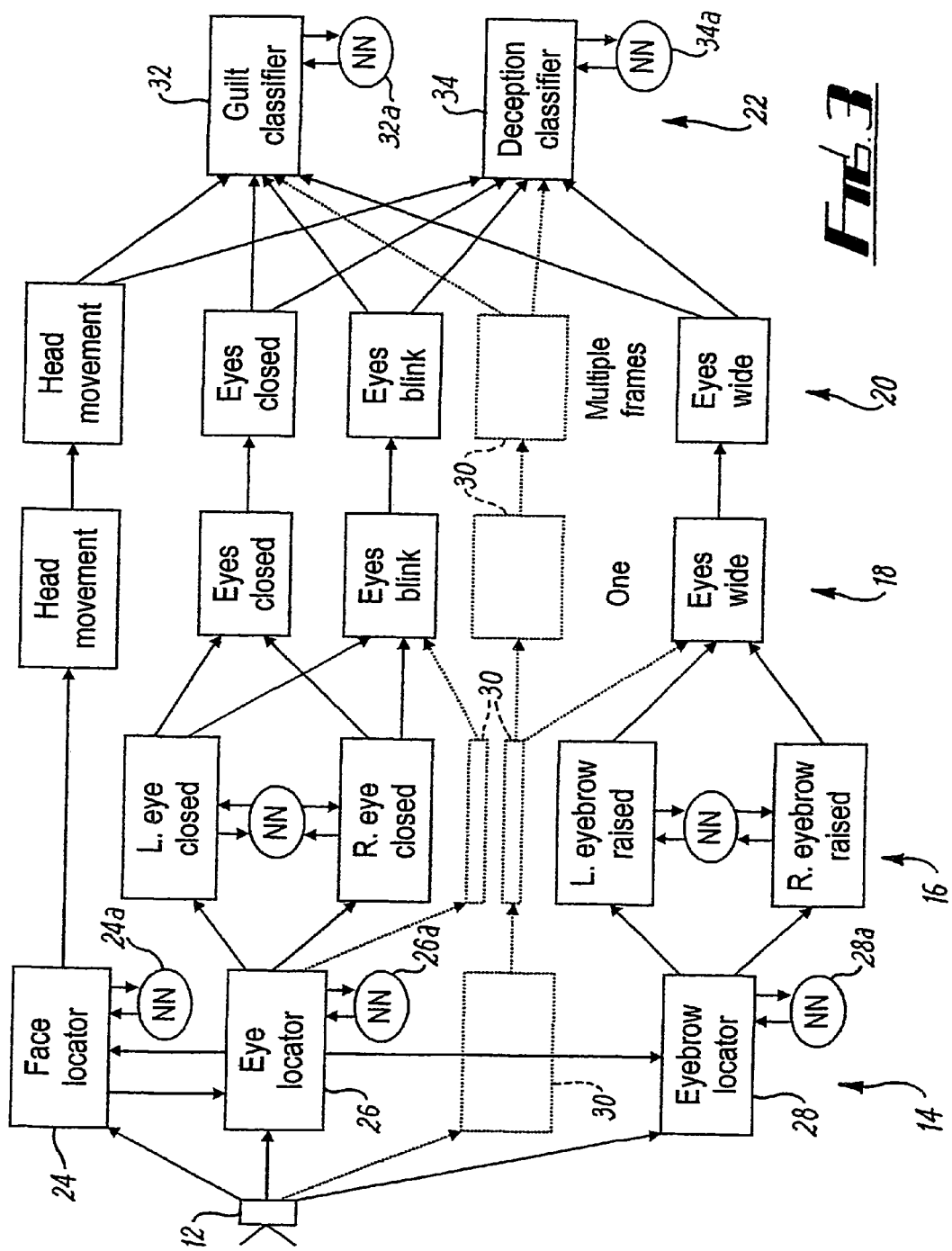
FIG. 3 is a schematic diagram showing elements of the object locator, pattern detector, channel coder, grouped-channel coder and classifiers overviewed in FIG. 2.

The present invention utilises artificial intelligence to analyse channels relating to the behaviour of the subject. In a preferred, but non-limiting, embodiment artificial neural networks are used.

A neural network is a massively parallel network of simple processors, or 'neurons', that have a capacity for storing experiential knowledge. Knowledge is acquired through training rather than programming and is stored in the connection strengths between neurons in the network (see, for example, Hassoun, M H, Fundamentals of Artificial Networks, 1995, MIT Press).

To such a machine-based system, the relative importance of channels does not matter, since the Neural Network accepts all channels provided and decides for itself which channels are important, unimportant or redundant. Initially in training, all channels effectively have the same importance, but as training progresses, the machine itself decides the level of importance for each channel. In general, the more people and channels that are used for training, the more accurate will be the subsequent results when the neural network is used to make assessments of previously unseen people. The neural network is able to detect patterns in data relating to a subject's behaviour even when there is a high dimensional input, i.e., when many channels are used. The channels are automatically weighted appropriately during training. Once trained, newly presented data patterns comprising the behaviour of the subject are classified quickly, and important patterns are not missed.

FIG. 1 depicts a general embodiment of an apparatus according to the present invention for the analysis of the behaviour of a subject The apparatus comprises:

detection means 12 for making one or more measurements or observations of the subject;

coding means 14, 16, 18, 20 for coding the measurements or observations into a plurality of channels and artificial intelligence means 22 adapted to analyse the channels and output information relating to the psychology of the subject.

FIG. 2 depicts a specific embodiment of an apparatus according to the present invention for the analysis of nonverbal, visual behaviour.

In the specific embodiment, the detection means 12 is a camera, such as a video camera, or a recorded frame sequence that can provide moving images of the subject in the form of a plurality of frames.

"Object locators" 14 find objects on the image, such as a face, eye, nose etc. 'Pattern detectors' 16 detect patterns within the object areas, for example a closed eye, squinting eye or eyeball looking to the left. In the specific embodiment these object locators and pattern detectors use trained neural networks 14a/16a. The channel coders 18 use data from the pattern detectors 16 and object locators 14 to automatically code the channel data. Grouped-channel coders 20 collate the data over a fixed or variable length of time to produce a scaled result.

In the specific embodiment, the classifier 22, which comprises neural networks 22a, uses the data from the grouped-channel coders 20 to make a final decision relating to the psychology of the subject.

FIG. 3 shows the hierarchy of the coding means 14, 16, 18, 20 and artificial intelligence means 22 in yet more detail. Identical numerals to FIG. 2 are used to denote elements such as the object locators 14, pattern detectors 16, channel coders 18, grouped-channel coders 20 and classifiers 22. These numerals identify the general location of these components in FIG. 3. Elements common to a component are arranged in the form of a vertical column above the relevant numeral in FIG. 3. Thus, for example, the object locator 14 comprises a number of individual elements such as a face locator 24, eye locator 26, and eyebrow locator 28, which in turn have an associated face locator neural network 24a, eye locator neural network 26a, and eyebrow locator neural network 28a. The specific elements shown in FIG. 3 are not exhaustive in respect of the level of processing complexity: other features may be detected and other channels may be coded. It is the purpose of the dotted elements 30 in FIG. 3 to denote such further processing elements. The channels from the grouped-channel coders 20 are fed to a guilty classifier 32 and a deception classifier 34. Each classifier has an associated neural network 32a, 34a Behaviour associated with guilt can appear similar to behaviour associated with deception, and such similarities have hampered the accuracy of some prior art deception detection systems, since guilty behaviour can lead to a "false positive" for deceptive behaviour. However, over a number of channels (such as the channels described herein) overall differences between guilty behaviour and deceptive behaviour are manifest. By providing a classifier 32 which is specifically trained to recognise guilty behaviour and a separate classifier 34 which is specifically trained to recognise deceptive behaviour, separation of guilty behaviour from deceptive behaviour is achieved. It is noted in passing that it is possible for a subject to be guilty and deceptive.

It will be apparent to the skilled reader that neural networks are used in three broad ways in this specific embodiment They are used for object location, object pattern recognition, and for classifying grouped channel data. The object location and object pattern recognition neural networks 14a, 16a are used to create channel data per frame and hence grouped channel data over a number of frames. The classifier neural network 22a uses the grouped channel data to make a decision about the subject's mental, behavioural and/or physical states.

The use of the neural networks represents an extremely powerful, flexible and quick way of performing the coding and analysing the coded channels. However, other ways of performing this function would occur to one skilled in the art, and so the use of neural networks (or other artificial intelligence techniques) for this purpose should not be considered to be a limiting aspect of the invention.

The non-limiting embodiment will be described in further detail below.

DETAILED DESCRIPTION OF A SPECIFIC EMBODIMENT OF THE APPARATUS

In the case of nonverbal visual behaviour, the detection means 12 is most likely a video camera. The frame sequence data is passed to the object locators.

Object Locators

The object locators extract predefined features from the frame sequence. An important object to be found is the face. Once the face is found, assumptions can be made about the approximate locations of the facial features and other body parts.

Locating a face in an image is a complex task. Images contain vast amounts of data that have to be handled. A face may appear anywhere in an image, at any scale and rotation. A person may wear make-up, glasses, have a beard or moustache or have a face-covering hat or hairstyle. The lighting level and direction may differ and the background may be complex. Additionally, the requirement for real-time channel coding and analysis necessarily means that the main objects have to be found quickly. There are various methods of achieving face detection.

In a current working arrangement two supervised learning neural networks are used to recognise the difference between a face and a non-face image. One network serves to compress the pixel data, the other serves to classify the compressed data. To train the networks, manually collected image sets are used—a set of face vectors and a set of non-face vectors. Once trained, the networks can classify a specific area from the frame as being a 'face' or 'non-face'.

Other objects such as the nose, mouth, eyebrows, hands etc can be found in a similar manner. Increasing the number of objects adds robustness to the system For example knowledge about the eyes allows the face location to be fine-tuned. Each object found helps to fine-tune the positions of other objects because, for example, facial features occur with relatively well-defined positional ratios and there are simple rules that can be followed—for example that the eyes are above the nose.

If one object is not located correctly, the results from the other objects could still provide a sensible answer. Neural networks are tolerant of slight pattern deviations. If there are many channels, based upon many objects, just one or two channel errors would have little effect.

Pattern Detectors

The pattern detectors recognise the patterns of known objects. For example, a neural network that has been trained to specifically recognise a 'closed eye' issues a '1' for a closed eye and a '−1' for an open eye. The eye object in compressed form is already available and this is used as input to each eye pattern detector, so each network is relatively small, thereby providing a speed advantage.

The pattern detectors are trained using a data set that exhibits large pattern variations for the particular object. In the specific embodiment discussed herein a 'multiple-choice' coding method is employed for each object pattern. This approach provides uncomplicated codes, and has the advantages that coders do not have to be trained and objects need not be facially based. However, the use of more sophisticated approaches such as Ekman's Facial Action Coding System (FACS) [Ekman, P., Friesen, W. V. (1978) Consulting Psychologists Press, Palo Alto, Calif., US] is within the scope of the invention. FACS is a thorough coding system which relates to muscle group movement in the face; a trained coder is required.

Extracting the Channel Data and Grouped Channel Data

The next stage is to extract channel information per frame. Such channels rely upon one or more object positions or pattern detectors. For each channel, the statistics from grouped channel data provide more information. Channel data may be collected in binary digital or analogue fashion. The channel may represent what is in the current frame or may represent the relationship between the current frame and one or more previous frames. An example of the latter is an eye blink. A particular channel signal may be binary in nature, e.g. '0' or '1', or "analogue", having one of a range of values, for example real numbers between '−1' and '1'. A single channel may also be represented by a binary or analogue collection of data, such as a small pixel area. For video images, there are three main types of channel extraction, henceforth termed basic, simple and complex.

Basic Channel

This type of channel either relies upon the relative object positions, changes in the object positions or basic functions operating upon the object pixels. For example, a 'head movement' channel may just rely upon the location of the face in each frame. Because the distance of each person to the camera may vary between videos and within a video, the positional measurements rely on a common measurement. The face width and height is used to determine the relative distances or movements. The values are normalised into a number between '−1' and '1'.

For simple distances between objects, (e.g. the hand and face) '−1' relates to the minimum chosen distance (e.g. 0 face widths) and '1' relates to the maximum chosen distance (e.g. 10 face widths). A hand covering the mouth or nose or close to the face may be a 'concealment' cue.

Alternatively both the vertical and horizontal distances could be measured between objects. A negative vertical value may show that object 'a' is above object 'b' whilst a positive value would show that object 'b' is above object 'a'. Negative numbers may show movement in one direction and positive numbers may show movement in the opposite direction.

An example of a basic function is a determination of the amount of redness in the face. This may take the red component of the face object and compare it to a previous frame, to see if there is any blushing or blanching. The result would be ranged between '−1' and '1' subject to some minimum and maximum criteria.

When grouping the data one or more channel statistics might be produced for an individual channel. For example, the mean, median and mode values may be produced from the valid data. Alternatively, the valid data may provide a single statistic—for example the percentage of 1's normalised into the range '−1' to '1'. Other transformations may be used to encode the data.

Simple Channel

This type of channel uses the pattern detectors and makes a simple decision for each frame. For example, an 'eyes closed' channel may rely on four results—left eye closed, right eye closed, left eye fully or half closed, right eye fully or half closed. Each network provides an output in the range '−1' to '1'. The channel may be an average of the network responses or may use some sort of logical decision. When grouping the results one or more statistics can be created per channel—e.g. the percentage of 1's nomalised into the range '−1' to '1'.

Complex Channel

This type of channel uses pattern detectors in a more complex manner. For example an eye blink may be deemed to occur when there is an eye closed immediately followed by an eye open. Knowledge may be used to prevent an eye blink being confused with the person looking at the floor or with a one-frame network error.

Obtaining the statistics is also more complex, because there are time related minimum and maximum values to consider. For the Simple channel, the minimum is a standard 0 per second and the maximum is a standard fps per frame, where fps is the frames per second. The Complex channel typically has a non-standard minimum and maximum. For example, the minimum for eye blinks can be set to 0 per second, and the maximum set to just 2 per second.

Grouped Channel Statistics

Channel signals are collected over a number of frames. One or more statistics can be collected for a particular channel, e.g., the percentage of 1's normalised into the range −1 to 1, mean values, average pixel arrays and the number of 1's related to a chosen maximum.

Statistics can be calculated for fixed time periods or for variable time periods, for example the time that relates to the specific answer to a question. In each case valid channel statistics are only calculated if the amount of valid data collected is greater than a set percentage.

If a particular object is not found in a particular frame, the object position is 'invalid', the pattern detectors that rely upon that object have 'invalid' results, and the channel output that relies upon the object is 'invalid'. The grouped channel statistics may however be 'valid' or 'invalid' depending upon the number of previous channel data results. In one embodiment, the amount of valid data collected has to be greater than 95%.

Collation of Channel Statistics

The statistics (in the range −1 to 1) from each channel are concatenated to produce a vector that represents all the channel statistics over the time period in question. Some vectors are stored for training and testing purposes. In use, other previously 'unseen' vectors will be classified Because some behaviours may have a slow pattern and others are fleeting (such as microexpressions), it may be advantageous to collate the channel statistics from one or more time periods to create the vector. Each channel may have its own optimum measurement time period.

Analysis of the Collated Channel Statistics

Collated channel statistic vectors are used to train neural networks to output information relating to the psychology of the subject when a previously unseen vector is presented.

Once trained and tested the network offers similar results for a similar situation with a similar group of people. A larger training set which contains more people, situations and behaviours would increase the generality of the network. A 'fine-tuned' training and testing set (e.g. male Caucasian psychopaths/non-psychopaths) would provide enhanced results for a specific study area.

The output of one or more classifier networks may provide an additional input to a different classifier network. For example, if the classifiers are 'deceptive answer', 'deceptive demeanor' and 'guilt', the output from the 'deceptive demeanor' network and 'guilt' networks may provide two additional inputs to the 'deceptive answer' network in an attempt to improve the performance of the latter.

The embodiment discussed above is an example only; the skilled reader will readily appreciate that many possibilities exist. Indeed, the approach described above is, in part, a consequence of the computing power available. Different feature extraction algorithms and/or neural networks might be used. Faster processing, perhaps using parallel processing, would be advantageous. Supporting hardware such as digital signal processors, neural network accelerators and analogue processing devices might be employed. Different forms of system access might be utilised—for example, remote access, such as via the Internet and observations utilised by the technique might be extended or replaced by using various sensors, such as a voice stress or pitch sensor, a microphone for paralanguage or verbal behaviours, a thermal imaging camera, ultrasound devices, load cells, microwave perturbation detectors and biological monitors such as a skin resistance monitor, a heartbeat monitor, blood pressure detector, breathing rate monitor and/or an EEG monitor. Verbal behaviour, i.e. the meaning of spoken words might be subjected to intelligent analysis. For example, the number of negative words such as "not", "never" and the numbers of possessive words such as "me", "mine" and "I" might be analysed Literature suggests that the number of negative words may increase with deception whereas the number of possessive words may decrease. Channels could be supplied in binary or analogue format via an interface such as a data logging device. Interaction with the subject might be varied by combining the technique with appropriate technologies such as a Conversational Agent (for example, "The Zen of Scripting Verbots"® virtual personalities Inc, VPI, Los Angeles, USA). A further possibility is to analyse more than one subject at once. Information might be gleaned from the way in which the subjects interact with each other, instead of, or in combination with, external stimuli.

Other artificial paradigms might be used in place of artificial neural networks, for example, unsupervised learning paradigms. Also, it will be apparent to the skilled reader that a variety of Neural Networks architectures may be used in different stages of the various embodiments of the apparatus described, and in other embodiments. Different channels might be analysed, and more of the subject's body, perhaps the entire body, might be recorded by one or more cameras in order to produce such channels.

The invention can be utilised for many purposes and is in no way limited to the detection of deceit and guilt. For example the invention might be used to assess whether a person is under stress at work, or to assess the aptitude of a subject for a specific task or role.

SPECIFIC EXAMPLE

In a confidential study, 41 volunteers from different ethnic backgrounds performed small tasks and were interviewed about these tasks. The data collection strategy was taken from nonverbal behaviour literature.

On arriving each volunteer was given an information sheet. This included the reasons for the study but also some information designed to improve their motivation to lie. For example it was stated that lying can be seen as a skill and that sometimes we have to deceive people for their own good. The volunteer was also told that their performance would be scrutinised by the interviewer, by their peers and by a computer. They were then asked to pick a random number out of a box and were asked to go into the interview room and read the instruction sheet.

The instruction sheet asked the subject to take a box from under the chair, look inside the box and to pick up/inspect the contents of the box. The box contained a pair of spectacles and a ten-pound note. If the subject had an odd number, the subject was required to put the money in their pocket (task one). If the subject had an even number, the subject was required to replace the money in the box (task two). The box was to be put back under the chair. Subjects were told that they were about to be interviewed about the location of the money and that they would be accused of taking the money. Subjects having the money in their pocket were instructed not to admit to it. Subjects were instructed to try to answer the questions in sentences, and to replace the instruction sheet.

A few minutes later the interviewer arrived. After a brief greeting the interviewer asked ten questions in order. At the time of the interviews the interviewer did not know whether a volunteer as lying or telling the truth in a particular interview.

At a later time, the interviewee performed the task which he/she had not performed earlier, and a second interview was commenced. Identical questions to the first interview, in identical order, were asked again. There were 78 useable videos.

Interviews were recorded by three video cameras with microphones. One camera recorded the head and shoulders of the interviewee, a second recorded the interviewee's full body and the third recorded the interviewer's movements. Both image and sound offered nonverbal channels. For each interview, the camera operator entered the room just before the interviewer to start the cameras. After the interviewer left the room, the cameras were stopped and the camera operator left the room.

In the present example, only the video of the subject's head and shoulders was used for analysis; sound was excluded from the analysis as well. It is within the scope of the invention to utilise the additional information contained within the other videos and the sound recordings.

Each video was digitised into an 15 frames per second AVI film using a low-cost capture card. Because a large quantity of data was produced, the capture parameters employed were the result of a compromise between quality and storage size. Video frames were 384 pixels wide by 288 pixels in height. 10 gray-scale frames were saved from each head and shoulder video image, giving 780 static frames. These were chosen such that there was a wide variation between the images.

From each frame the top section of the facial area (the eyes and nose) was manually extracted such that the line joining the eyes was horizontal and the distance between the eyes was scaled. The resulting image was cropped. Literature shows that the eyes and nose area can be used to detect faces. The cropped images were shrunk to 12 pixels wide by 10 pixels high with 8 pixels between the eye centres. The small size increases the search speed, is tolerant of positional errors and yet provides a reliable face/non-face decision. The shrunken images were histogram normalised, smoothed, copied and mirrored so that a face data set of 1560 was achieved. 7800 'non-face' images were extracted randomly from the whole frames, particularly the head area. These images are also shrunk, histogram normalised and smoothed.

The images were converted into 120-element vectors with normalised elements in the range −1 to 1 by concatenating each row of the pixel matrix and by using the simple function $F(x)=(x*2/255)-1$.

One neural network was trained to provide a low dimensional representation of a face; another was trained to classify low dimensional representations as faces or non-faces. Both networks were fully-connected three layer networks, each with a bias and were trained using a straight forward back-propagation algorithm, with a bipolar sigmoid squashing function. Back-propagation networks are a common type of network well known to those skilled in the art (see, for example, Hassoun, M H, ibid).

One of the networks was a 'compression' style network, having the same number of outputs as inputs (120) but a small number (14) neurons in the hidden layer. The network weights were initialised to small random values and, by using gradient descent to adjust the weights as training progressed, the compression network was encouraged to restore the image at the output level. Back-propagation attempts to extract the regularities (significant features) from the input vectors to allow successful restoration of the image at the output layer. The hidden layer evolved a low dimensional distributed representation of the face training data.

The function of the compression was twofold. First, use of the compressed representations decreases the number of inputs and hence connections for the face detection network, allowing faster learning and relearning of face detection with different face/non-face subsets. Also, while simple gray levels may adequately represent changes in face images for part of a single face in fixed lighting, the representations of multiple faces benefit from preprocessing, enabling essential properties to be extracted.

After the compression network had been trained, the face and non-face images were passed through the network and the 14-element vectors at the hidden layer were recorded. These vectors, which also have elements ranging between '−1' and '1', were then used to train and test the face detection network. The face detection network contained 6 neurons at the hidden layer and just one output neuron. The network was encouraged to produce a '1' for a face and '−1' for a non-face.

Once the networks were trained a face could be detected in a video frame. Areas of movement, edges or areas of high contrast identified an initial search area. At different scales, a window was passed over the initial search area starting at the centre and spiralling outward. A 120-element vector was produced for each window position by shrinking, histogram normalising, smoothing and ranging the window contents. This vector was presented to the trained compression network to produce a 14-element vector. This in turn was presented to the face detection network. If the output surpassed a limit value (0.997 was used in a specific embodiment), a face was considered to be found and the search was stopped. At the position found, faces of slightly different scales were tested, and the best face was chosen.

For the next frame, a new search area was based upon the facial area and scale found in the previous frame plus a user definable border size. Again, the search proceeded in a spiral fashion starting at the centre. A faster frame rate and an intelligent estimation of the face speed and direction would improve the face tracing capabilities.

When the face was not found, the search area remained the same and the next frame was tested. If the face was not found for a few frames, this did not affect the overall result. This is because the channel statistics depend upon results from many frames. This is especially true when nonverbal nonvisual and verbal channels are available. If the face was not found for many frames, then the percentage of valid data becomes small and the main classifier provides a result deemed to be 'unknown'.

Once the face was found assumptions could be made about the relative size and location of the facial features and the rough location of the torso.

For example, the location of the eyes was detected in much the same way as the head. In this case 4680 16×12 eye training images were manually extracted from higher resolution static 48×40 face images.

Since the face had already been found, a fairly accurate initial location of each eye was already known. The face location was determined using a 12×10 scaled window. An eye location scaled window of 16×12 provided a more accurate eye locator. An initial location was estimated, and the search proceeded in a spiral fashion. The search area was fairly constrained When the eye was found conclusively, for example by a network output of 0.99, the search was stopped. Otherwise three possible options could be used. In one option, the 'best' eye within the area was chosen e.g. a network may have given an output of 0.8. This was probably an eye but with a lower confidence level. However, because it came from the area containing a face and was close to where an eye was expected it was likely to be an eye. In a second option, the eye position as determined by the face locator was chosen. In the third option, the eye position was considered to be invalid. All channels relying upon the eye network would thus be invalid.

In the specific experiment, the eyebrow object locators and the nose object locator were also used to help determine whether a valid eye was found. Right eye and right eyebrows were detected by mirroring the pixels and passing this to the left eye and left eyebrow object locators The pattern detectors were initially based upon the eye patterns. Three multiple-choice questions were asked for each eye object—

| Q1 Openness of the eye? | Q2 Horizontal gaze? | Q3 Vertical gaze? |
| --- | --- | --- |
| Eye wide open | Eye fully right | Eye fully up |
| Eye slightly wide | Eye partly right | Eye partly up |
| Eye normal open | Eye horizontally central | Eye vertically central |
| Eye partly closed | Eye partly left | Eye partly down |
| Eye fully closed | Eye fully left | Eye fully down |
| Eye partly squinting | | |
| Eye fully squinting | N/A (eye fully closed/squinting) | N/A (eye fully closed/squinting) |

An eye that was looking up and to the left produced the following 'answer':
Q1: Eye normal open; Q2: Eye fully left; Q3: Eye fully up For the eyes, there were 17 eye classifications from the multiple-choice questions. 17 different basic networks were trained and tested using the 4680 manually classified eyes. For example, the 'eye fully right' network was trained so that eyes looking fully to the right were trained as '1' and all the other eyes in the data set i.e. eye partly right, eye horizontally central, eye partly left, eye fully left and N/A were trained as '−1'. In this scheme, if a network was trained to recognise an eye looking right this included eyes looking down/right and up/right. Other networks were also trained such as 'fully or partly right' which helped to add robustness to the next stage. Networks were trained in much the same way as the eye/non-eye network.

In this experiment the following channels were selected:

| | | |
| --- | --- | --- |
| Sex | Known | −1 or 1 |
| Planned or unplanned interview | Known | −1 or 1 |
| Face vertical movement | Basic | −1 to 1 |
| Face horizontal movement | Basic | −1 to 1 |
| Facial skin movement | Basic | −1 to 1 |
| Face scale (forward/backward) | Basic | −1 to 1 |
| Left eye - looking left | Simple | −1 to 1 |
| Left eye - looking right | Simple | −1 to 1 |
| Left eye - closed | Simple | −1 to 1 |
| Left eye - blinking | Complex | −1 to 1 |
| Right eye - looking left | Simple | −1 to 1 |
| Right eye - looking right | Simple | −1 to 1 |
| Right eye - closed | Simple | −1 to 1 |
| Right eye - blinking | Complex | −1 to 1 |

Movements and distances were simply assigned a value of 1 if above a certain level, and −1 if below. When grouping the data the percentage of 1's was normalised into the range −1 to 1. For the simple channels e.g. the eye closed channel, a logical decision was made based upon a number of pattern detectors. Again, when grouping the data the percentage of 1's was normalised into the range −1 to 1. The complex 'blinking' channels used outputs from the pattern detectors from the current and previous frames along with knowledge about the frequency of eye-blinks in humans.

Statistics were collected for the whole of each answer given by a person and for fixed, overlapping 3-second time periods. An answer was deemed to start from 1 second before a subject started to move his/her mouth to 2 seconds after the mouth ceased to move. For each channel a multiple-element storage area was created large enough for the time period. Each single element held the channel data for one frame. Each location in the storage area, one per frame, was initially set to 'invalid' by an '88' being stored in every location. For each new frame processed, if the objects required for the channel were found the channel data was added to the next storage location otherwise an '88' was added to the next storage location.

When each storage location had been addressed, the statistics of the elements were calculated. The channel statistics were calculated whenever a new frame occurred if the amount of valid data in the storage area was greater than 95%. For a 3-second time period the storage area held data for 45 frames, because the video frame rate was 15 frames per second. A statistic is produced only in the instance that 95% or greater of the data are valid (i.e. between 43 and 45 valid frames).

40% of the collated channel statistics were used to train three fully connected, 3-layer back-propagation classification networks. 20% of the collated channel statistics were used for validation purposes, the remaining 40% was used for testing. The classification networks were trained to detect deception periods, feelings of guilt and whether the whole interview was generally deceptive. Each network had as input a 14-element input vector, around 8 neurons in a hidden layer and 1 neuron in the output layer.

When the channel statistics were accumulated over the length of the answer, a clear classification was known for most answers: the answer was either the truth or a lie.

When the channel statistics were accumulated over the 3-second time periods, there were three considerations. Firstly, some of the time periods related to instances where the person was being deceptive and thus the desired output was '1'. Other periods represented when the person was being truthful (−1). Some periods, however, were on the cross-over point. Since the desired output was in the range '−1' to '1', if 1.5 seconds were truthful and, 1.5 seconds were deceptive the desired output was '0'.

The second consideration was how to deal with 'gaps' between answers. These vectors were ignored, but an alternative strategy would be to set the 'desired output' as 0. Other strategies are possible.

The third consideration was that, since answers were deemed to start 1 second before the person started talking and 2 seconds after they stopped talking, two answers sometimes overlapped. If one answer was truthful and the other was deceptive, two vectors were produced for the same time-period, but one vector would be defined as truthful and other would be defined as deceptive. These were permitted because generally there were few of these vectors created. By dealing with this situation in a more rigorous fashion, both the training and testing results would be improved.

Typically, the results were well above chance level. Early experiments with this channel set and a slightly expanded set provided deception detection to an accuracy of 75-85%.

The invention claimed is:

1. An apparatus for automatically analysing the behaviour of a subject, the apparatus comprising:
    a detector for making one or more non-invasive visual observations of the subject each consisting of a plurality of measurements over a given period of time, wherein the detector comprises a camera providing images of the subject in the form of a plurality of frames;
    a coder comprising (i) object locators configured to extract predefined features from the plurality of frames, (ii) pattern detectors configured to recognise a plurality of patterns for each of the features extracted by the object locators, (iii) channel coders for coding the data from the object locators and pattern detectors into a plurality of channels, each channel comprising channel information for each of the plurality of frames and (iv) grouped-channel coders for collating data from each of said channels to produce a vector, said vector comprising a plurality of vector elements, each of said vector elements being associated with a respective one of said plurality of channels and being based upon said channel information for the respective channel for each of the plurality of frames, such that said vector represents channel statistics over a period of time in which said one or more non-invasive visual observations of the subject are made; and
    an automatic machine classifier adapted to analyse the vector and output information relating to the psychology of the subject.

2. The apparatus of claim 1, wherein the automatic machine classification means comprises artificial intelligence means or statistical classification means.

3. The apparatus of claim 1 wherein object locators and pattern detectors use trained neural networks; and
    the automatic machine classifier comprises neural networks.

4. The apparatus of claim 1, wherein the camera is a video camera.

5. The apparatus of claim 1, wherein the channel coders use data from the object locators and pattern detectors to automatically code the data into the plurality of channels.

6. The apparatus of claim 1, wherein the grouped-channel coders collate the data from the object locators and pattern detectors over a fixed or variable length of time to produce a scaled result.

7. The apparatus of claim 1, wherein a channel represents what is in a current frame.

8. The apparatus of claim 1, wherein a channel represents the relationship between the current frame and one or more previous frames.

9. The apparatus of claim 1, wherein at least one channel is a basic channel which relies upon relative object positions, changes in the object positions or basic functions operating upon the object pixels.

10. The apparatus of claim 1, wherein at least one channel is a simple channel which uses the pattern detectors and makes a simple decision for each frame.

11. The apparatus of claim 1, wherein the object locators comprise face, eye and/or eyebrow locators which each have an associated artificial neural network.

12. The apparatus of claim 1, wherein the automatic machine classifier comprises a guilty classifier and a deception classifier, each classifier comprising a trained artificial neural network to make a high-level classification of a subject's behaviour as deceptive and/or guilty.

13. A method for analysing the behaviour of a subject, the method comprising:
    making, using a camera, one or more non-invasive visual observations of the subject each consisting of a plurality of measurements over a given period of time, wherein the observations are made by taking one or more images of the subject so as to provide a plurality of frames;
    coding the observations into a plurality of channels, wherein the coding comprises the steps of (i) extracting predefined features from plurality of frames using object locators, (ii) recognising a plurality of patterns for each of the extracted predefined features using pattern detectors, (iii) coding the data from the object locators and pattern detectors into the plurality of channels, each channel comprising information for each of the plurality of frames and (iv) collating data from each channel to produce a vector, said vector comprising a plurality of vector elements, each of said vector elements being associated with a respective one of said plurality of channels and being based upon said channel information for the respective channel for each of the plurality of frames, such that said vector represents channel statistics over a period of time in which said one or more non-invasive visual observations or the subject are made; and
    analysing the vector using an automatic machine classifier to make a high-level classification of the subject's behaviour and to output information related to the high-level classification.

14. The method of claim 13 wherein the object locators and pattern detectors use trained neural networks.

15. The method of claim 13, wherein the automated machine classifier uses a neural network.

16. The method of claim 13, wherein the deceptive behaviour of the subject comprises lying in an interview scenario.

17. The method of claim 13, wherein the step of coding the data into the plurality of channels uses channel coders and the step of collating data from each channel to produce a vector that represents all the channel statistics over the given period of time uses grouped-channel coders.

18. The method of claim 17, wherein the channel coders automatically code the data from the object locators and pattern detectors into the plurality of channels.

19. An method according to claim 17, wherein the grouped-channel coders collate the data from the object locators and pattern detectors over a fixed or variable length of time to produce a scaled result.

20. The method of claim 13, wherein a channel represents what is in the current frame.

21. The method of claim 13, wherein a channel represents the relationship between the current frame and one or more previous frames.

22. The method of claim 13, wherein at least one channel is a basic channel which relies upon relative object positions, changes in the object positions or basic functions operating upon object pixels.

23. The method of claim 13, wherein at least one channel is a simple channel which uses the pattern detectors and makes a simple decision for each frame.

24. The method of claim 13, wherein the object locators locate the face, eye and/or eyebrow on the plurality of frames.

25. The method of claim 13, further comprising the step of analysing the channels to make a high-level classification of a subject's behaviour as deceptive and/or guilty.

26. A lie detector apparatus for automatically analysing the behaviour of a subject, the apparatus comprising:
   a detector for making one or more non-invasive visual observations of the subject each consisting of a plurality of measurements over a given period of time, wherein the detector comprises one or more cameras providing images of the subject in the form of a plurality of frames;
   a coder comprising (i) object locators configured to extract predefined features from the plurality of frames, (ii) pattern detectors configured to recognise a plurality of patterns for each of the features extracted by the object locators, (iii) channel coders for coding the data from the object locators and pattern detectors into a plurality of channels, each channel comprising channel information for each of the plurality of frames and (iv) grouped-channel coders for collating data from each of said channels to produce a vector, said vector comprising a plurality of vector elements, each of said vector elements being associated with a respective one of said plurality of channels and being based upon said channel information for the respective channel for each of the plurality of frames, such that said vector represents channel statistics over a period of time in which said one or more non-invasive visual observations of the subject are made; and
   an automatic machine classifier adapted to analyse the vector and output information relating to the deceptive nature of the subject.

27. An apparatus for automatically analysing the behaviour of a subject, the apparatus comprising:
   a detector for making one or more non-invasive visual observations of the subject each consisting of a plurality of measurements over a given period of time, wherein the detector comprises a camera providing images of the subject in the form of a plurality of frames;
   a coder comprising (i) object locators configured to extract predefined features from the plurality of frames, (ii) pattern detectors configured to recognise a plurality of patterns for each of the features extracted by the object locators, (iii) channel coders for coding the data from the object locators and pattern detectors into a plurality of channels, each channel comprising channel information for each of the plurality of frames and each channel representing a pattern for a feature extracted by the object locators and (iv) grouped-channel coders for collating data from each of said channels to produce a vector, said vector comprising a plurality of vector elements, each of said vector elements being associated with a respective one of said plurality of channels and being based upon said channel information for the respective channel for each of the plurality of frames, such that said vector represents channel statistics over a period of time in which said one or more non-invasive visual observations of the subject are made; and
   an automatic machine classifier adapted to analyse the vector and output information relating to the psychology of the subject.

28. A method for analysing the behaviour of a subject, the method comprising:
   making, using a camera, one or more non-invasive visual observations of the subject each consisting of a plurality of measurements over a given period of time, wherein the observations are made by taking one or more images of the subject so as to provide a plurality of frames;
   coding the observations into a plurality of channels, wherein the coding comprises the steps of (i) extracting predefined features from plurality of frames using object locators, (ii) recognising a plurality of patterns for each of the extracted predefined features using pattern detectors, (iii) coding the data from the object locators and pattern detectors into the plurality of channels, each channel comprising information for each of the plurality of frames and each channel representing a pattern for a feature extracted by the object locators and (iv) collating data from each channel to produce a vector, said vector comprising a plurality of vector elements, each of said vector elements being associated with a respective one of said plurality of channels and being based upon said channel information for the respective channel for each of the plurality of frames, such that said vector represents channel statistics over a period of time in which said non-invasive visual observations of the subject are made; and
   analysing the vector using an automatic machine classifier to make a high-level classification of the subject's behaviour and to output information relate to the high-level classification.

* * * * *